(12) United States Patent
Huke

(10) Patent No.: US 11,701,565 B2
(45) Date of Patent: Jul. 18, 2023

(54) SYSTEM FOR PLANNING, MANAGING, AND ANALYZING SPORTS TEAMS AND EVENTS

(71) Applicant: AdrenalineIP, Washington, DC (US)

(72) Inventor: Casey Alexander Huke, Washington, DC (US)

(73) Assignee: AdrenalineIP, Washington, DC (US)

( * ) Notice: Subject to any disclaimer, the term of this patent is extended or adjusted under 35 U.S.C. 154(b) by 0 days.

(21) Appl. No.: 17/712,320

(22) Filed: Apr. 4, 2022

(65) Prior Publication Data

US 2022/0226714 A1 Jul. 21, 2022

Related U.S. Application Data

(63) Continuation of application No. 16/752,894, filed on Jan. 27, 2020, now Pat. No. 11,298,605, which is a
(Continued)

(51) Int. Cl.
| | | |
|---|---|---|
| A63B 71/06 | (2006.01) | |
| A63B 43/00 | (2006.01) | |
| G06Q 10/06 | (2023.01) | |
| G06Q 10/0639 | (2023.01) | |
| A63B 102/18 | (2015.01) | |
| G16H 40/63 | (2018.01) | |
| G16H 40/20 | (2018.01) | |
| G16H 20/30 | (2018.01) | |

(52) U.S. Cl.
CPC ........ *A63B 71/0616* (2013.01); *A63B 43/004* (2013.01); *A63B 71/0622* (2013.01); *G06Q 10/06* (2013.01); *G06Q 10/0639* (2013.01); *A63B 71/0605* (2013.01); *A63B 2102/18* (2015.10); *A63B 2225/50* (2013.01); *A63B 2225/54* (2013.01); *A63B 2243/007* (2013.01); *A63B 2243/0025* (2013.01); *A63B 2243/0037* (2013.01); *G16H 20/30* (2018.01); *G16H 40/20* (2018.01); *G16H 40/63* (2018.01)

(58) Field of Classification Search
CPC ............ A63B 71/0616; A63B 71/0622; A63B 43/004
See application file for complete search history.

(56) References Cited

U.S. PATENT DOCUMENTS

| | | |
|---|---|---|
| 4,953,873 A | 9/1990 | Jacobson |
| 5,120,076 A | 6/1992 | Luxenberg et al. |
| (Continued) | | |

OTHER PUBLICATIONS

Kite, "Three Things Every Football Coach Should Know", Esquire Magazine, Dec. 1, 2006, retrieved from the Internet < http://www.esquire.com/features/ESQ1206FOOTBALL_214>; 1 page.
(Continued)

*Primary Examiner* — James S. McClellan
(74) *Attorney, Agent, or Firm* — Maier & Maier, PLLC

(57) ABSTRACT

A system for planning, managing, and analyzing sports teams and events. The system may include a content management function for storing data. The data can pertain to a plurality of sports-related statistics and a variety of identifying data. The system and method can also include an event management function for planning and evaluating sports-related events such as practices and games. The system and method can also include a report function which can provide a variety of statistical analyses.

7 Claims, 11 Drawing Sheets

Related U.S. Application Data continuation of application No. 16/354,435, filed on Mar. 15, 2019, now Pat. No. 10,583,345, which is a continuation-in-part of application No. 15/852,555, filed on Dec. 22, 2017, now abandoned, which is a continuation-in-part of application No. 13/614,257, filed on Sep. 13, 2012, now abandoned.

(60) Provisional application No. 61/565,042, filed on Nov. 30, 2011.

(56) References Cited

U.S. PATENT DOCUMENTS

| | | | |
|---|---|---|---|
| 5,772,512 | A | 6/1998 | Chichester |
| 6,406,372 | B1 | 6/2002 | Turmell et al. |
| 2002/0132211 | A1 | 9/2002 | August et al. |
| 2005/0112536 | A1 | 5/2005 | Frayman |
| 2006/0247808 | A1 | 11/2006 | Robb |
| 2008/0051201 | A1 | 2/2008 | Lore |
| 2008/0140233 | A1* | 6/2008 | Seacat .................. G06Q 90/00 700/91 |
| 2009/0064020 | A1* | 3/2009 | Morris ................ G06F 3/0481 715/765 |
| 2010/0137057 | A1 | 6/2010 | Fleming |
| 2010/0179930 | A1 | 7/2010 | Teller et al. |
| 2011/0183734 | A1 | 7/2011 | Koivisto et al. |

OTHER PUBLICATIONS

Notification of Transmittal of the International Search Report and the Written Opinion of the International Searching Authority dated Jul. 1, 2020, in connection with corresponding international Application No. PCT/US2020/034195 (7 pp.).

* cited by examiner

Fig. 9

Practice Script Template

Drill: Team  
Practice #: 5  
Date: August 15  
Period: 3

| # | FP | DOWN | DISTANCE | W8 | PER | PLAY CALL | FRONT | BLITZ | COVER |
|---|---|---|---|---|---|---|---|---|---|
| 1 Left | -1 | 1st | 10 | | 1 Wolf | Wing 323 Slice | Blue | | high |
| 2 Middle | -15 | 2nd | 5 | | 60 Bear | Spread Rt 65 X/Z-Out | Purple | Dog | bubble |
| 3 Right | -20 | 3rd | 2 | | 52 Orange | Twins Rt 23 Whip Read X-Smoke | Blue | Lightning | house |
| 4 Right | -33 | 1st | 10 | | 13 Lion | 448 Flame H-Leak (Kill 23) | Blue | | bubble |
| 5 Left | -46 | 1st | 10 | | 19 Cat | Clown Over 4 Hippo 48 Force | Crimson | | high |
| 6 Middle | 46 | 2nd | 5 | | 5 Eagle | Wing 324 Spark X-Smoke (Kill 24 Whip) | Grey | Lightning | high |
| 7 Middle | 40 | 3rd | 4 | | 46 Gator | 956 Expo (Kill Choice) | Purple | Dog | house |
| 8 Right | 10 | 1st | 3 | | 12 Lion | 447 Arc (Kill 48 Arc) | Blue | | tight |
| 9 Middle | 1 | 1st | 1 | | 26 Tiger | 695 Qk Choice X-Gift | Crimson | Pack | tight |
| 10 | | | | | | | | | |
| 11 | | | | | | | | | |
| 12 | | | | | | | | | |
| 13 | | | | | | | | | |
| 14 | | | | | | | | | |
| 15 | | | | | | | | | |
| 16 | | | | | | | | | |
| 17 | | | | | | | | | |
| 18 | | | | | | | | | |
| 19 | | | | | | | | | |
| 20 | | | | | | | | | |
| 21 | | | | | | | | | |
| 22 | | | | | | | | | |
| 23 | | | | | | | | | |
| 24 | | | | | | | | | |
| 25 | | | | | | | | | |

← 902 ← 904 ← 906 ← 908 ← 910 ← 912 ← 914 ← 916 ← 918 ← 920 ← 922

SYSTEM FOR PLANNING, MANAGING, AND ANALYZING SPORTS TEAMS AND EVENTS

CROSS-REFERENCE APPLICATIONS

The present invention claims priority under 35 U.S.C. § 120 to U.S. Provisional Patent Application No. 61/565,042, filed on Nov. 30, 2011 entitled "THE EDGE", the contents of which is incorporated by reference herein in its entirety, as well as U.S. patent application Ser. No. 16/752,894, filed on Jan. 27, 2020, U.S. patent application Ser. No. 16/354,435, filed on Mar. 15, 2019, U.S. patent application Ser. No. 15,852,555, filed on Dec. 22, 2017, U.S. patent application Ser. No. 13/614,257, filed on Sep. 13, 2012, the contents of which are also incorporated by reference herein in its entirety.

BACKGROUND

In sporting events, the slightest advantage may be the difference between a win and a loss. As a result, coaches have often employed statistical analyses in order to try to learn the tendencies of opponents and the effectiveness of various strategies and tactics. Tracking all of the data required to make these determinations is extremely time and resource consuming. Due to the time it takes to analyze statistical sports-related data, coaches are usually required to wait until the conclusion of a match or half in order to determine tendencies and strategic advantages.

While there are tools available for statistical analysis, many of these tools require extensive technology not compatible with an arena, stadium, or field on which most athletic contests are conducted. Additionally, these tools remain cumbersome to use before and after such contests as well, frustrating efficient game analysis and preparation. Further, many of these systems are not sports-specific and thus require tedious data entry, manipulation, and other time consuming actions in order to perform an analysis.

Additionally, although coaches and players watch film to review plays and perform assessments, the methods of reviewing and formatting the data are typically incomplete or riddled with errors. Errors occur based on handwritten or typed notes where any mistake in player number, formation, package, down, score, or any other situational information is improperly entered. These errors render any analytics derived therefrom as meaningless or worse, where they negatively impact review and strategy.

Additionally, known methods of reviewing and performing analytics are slow, time consuming, and/or impossible to utilize in real time or even time between games. There is no known method or system that can review and analyze data in real time or otherwise rapidly so that play suggestions can be made or success rates can be determined. Moreover, there is no known system or capability for properly storing and analyzing historical data in order to provide any meaningful outputs to coaches, players, or teams.

Further, play data stored in a database is impossible for a coach, player, or other reviewer to utilize without a direct comparison or each play, the players involved in each play, the situational data associated with each play, and the results of each play. Such data is not presently stored in a database in a manner that makes it accessible or usable. Further, the information cannot be translated into a usable or valuable form presently.

Thus, a system which provides quick, simple and efficient sports-specific statistical analysis on computing devices is desired.

SUMMARY

A sports management system, which can include a user interface, a processor, a memory, and a management module stored on the memory. The management module can be configured to receive and store data input by the user relating to sports plays and the results of implementing the sports plays, analyze the data input by the user, and provide the user with feedback and suggestions based on the analysis conducted.

BRIEF DESCRIPTION OF THE DRAWINGS

Advantages of embodiments of the present invention will be apparent from the following detailed description of the exemplary embodiments. The following detailed description should be considered in conjunction with the accompanying figures in which:

FIG. 9 is an exemplary embodiment of a practice script.

DETAILED DESCRIPTION

Aspects of the present invention are disclosed in the following description and related figures directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage, or mode of operation.

Further, many of the embodiments described herein are described in terms of sequences of actions to be performed by, for example, elements of a computing device. It should be recognized by those skilled in the art that the various sequence of actions described herein can be performed by specific circuits (e.g., application specific integrated circuits (ASICs)) and/or by program instructions executed by at least one processor. Additionally, the sequence of actions described herein can be embodied entirely within any form of computer-readable storage medium such that execution of the sequence of actions enables the processor to perform the functionality described herein. Thus, the various aspects of the present invention may be embodied in a number of different forms, all of which have been contemplated to be within the scope of the claimed subject matter. In addition, for each of the embodiments described herein, the corresponding form of any such embodiments may be described herein as, for example, "a computer configured to" perform the described action.

Generally referring to FIGS. 1-6, a system for identifying, organizing, storing and evaluating sports-related data may be disclosed. The system may be able to accept inputs relating to plays, statistics and other sports related data and may present a user with strategic or coaching options based on such inputs. The system may determine successful plays or systems based on prior actions or schemes. The system may also sort plays based on a variety of criteria, such as, but not limited to, effectiveness, situations and formations. The system may be implemented through any desirable operating system being run on any desirable computer interface, such as a computer, tablet or other personal computing device. In some exemplary embodiments, the system can network this data, which can allow users of the system to compare different teams and draw statistical analysis from the networked data.

Figure 1:
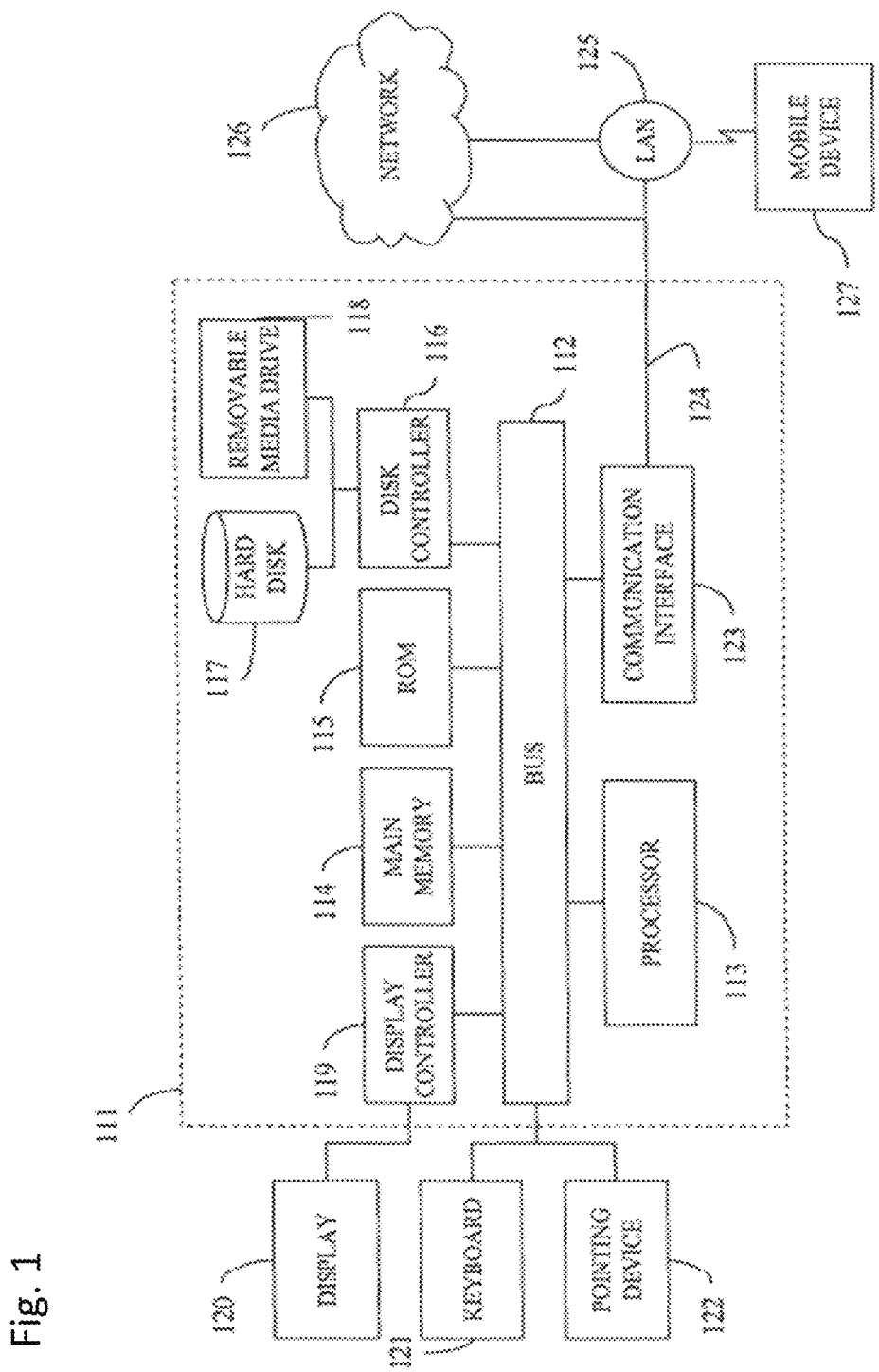
FIG. 1 is a diagram of an exemplary computer system.

FIG. 1 illustrates an exemplary computer system 111 upon which an embodiment of the present invention may be implemented. The computer system 111 includes a bus 112 or other communication mechanism for communicating information, and a processor 113 coupled with the bus 112 for processing the information. The computer system 111 also includes a main memory 114, such as a random access memory (RAM) or other dynamic storage device (e.g., dynamic RAM (DRAM), static RAM (SRAM), and synchronous DRAM (SDRAM)), coupled to the bus 112 for storing information and instructions to be executed by processor 113. In addition, the main memory 114 may be used for storing temporary variables or other intermediate information during the execution of instructions by the processor 113. The computer system 111 further includes a read only memory (ROM) 115 or other static storage device (e.g., programmable ROM (PROM), erasable PROM (EPROM), and electrically erasable PROM (EEPROM)) coupled to the bus 112 for storing static information and instructions for the processor 113.

The computer system 111 also includes a disk controller 116 coupled to the bus 112 to control one or more storage devices for storing information and instructions, such as a magnetic hard disk 117, and a removable media drive 118 (e.g., floppy disk drive, read-only compact disc drive, read/write compact disc drive, compact disc jukebox, tape drive, and removable magneto-optical drive). The storage devices may be added to the computer system 111 using an appropriate device interface (e.g., small computer system interface (SCSI), integrated device electronics (IDE), enhanced-IDE (E-IDE), direct memory access (DMA), or ultra-DMA).

Further, exemplary embodiments include or incorporate at least one database which may store software, descriptive data, system data, digital images and any other data item required by the other components necessary to effectuate any embodiment of the present system known to one having ordinary skill in the art. The database may be provided, for example, as a database management system (DBMS), a relational database management system (e.g., DB2, ACCESS, etc.), an object-oriented database management system (ODBMS), a file system or another conventional database package as a few non-limiting examples. The database can be accessed via a Structure Query Language (SQL) or other tools known to one having skill in the art.

Still referring to FIG. 1, the computer system 111 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 111 may also include a display controller 119 coupled to bus 112 to control a display 120, such as a cathode ray tube (CRT), liquid crystal display (LCD) or any other type of display, for displaying information to a computer client. The computer system includes input devices, such as a keyboard 121 and a pointing device 122, for interacting with a computer client and providing information to the processor 113. Additionally, a touch screen could be employed in conjunction with display 120. The pointing device 122, for example, may be a mouse, a trackball, or a pointing stick for communicating direction information and command selections to the processor 113 and for controlling cursor movement on the display 120. In addition, a printer may provide printed listings of data stored and/or generated by the computer system 111.

The computer system 111 performs a portion or all of the processing steps of the invention in response to the processor 113 executing one or more sequences of one or more instructions contained in a memory, such as the main memory 114. Such instructions may be read into the main memory 114 from another computer readable medium, such as a hard disk 117 or a removable media drive 118. One or more processors in a multi-processing arrangement may also be employed to execute the sequences of instructions contained in main memory 114. In alternative embodiments, hard-wired circuitry may be used in place of or in combination with software instructions. Thus, embodiments are not limited to any specific combination of hardware circuitry and software.

As stated above, the computer system 111 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 111, for driving a device or devices for implementing the invention, and for enabling the computer system 111 to interact with a human client. Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 113 for execution. A computer readable medium may take many forms, including but not limited to, non-volatile media, volatile media, and transmission media. Non-volatile media includes, for example, optical, magnetic disks, and magneto-optical disks, such as the hard disk 117 or the removable media drive 118. Volatile media includes dynamic memory, such as the main memory 114. Transmission media includes coaxial cables, copper wire and fiber optics, including the wires that make up the bus 112. Transmission media also may also take the form of acoustic or light waves, such as those generated during radio wave and infrared data communications.

Various forms of computer readable media may be involved in carrying out one or more sequences of one or more instructions to processor 113 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 111 may receive the data on the telephone line and use an infrared transmitter to convert the data to an infrared signal. An infrared detector coupled to the bus 112 can receive the data carried in the infrared signal and place the data on the bus 112. The bus 112 carries the data to the main memory 114, from which the processor 113 retrieves and executes the instructions. The instructions received by the main memory 114 may optionally be stored on storage device 117 or 118 either before or after execution by processor 113.

The computer system 111 also includes a communication interface 123 coupled to the bus 112. The communication interface 123 provides a two-way data communication coupling to a network link 124 that is connected to, for example, a local area network (LAN) 125, or to another communications network 126 such as the Internet. For example, the communication interface 123 may be a network interface card to attach to any packet switched LAN. As another example, the communication interface 123 may be a wireless link. In any such implementation, the communication interface 123 sends and receives electrical, electromagnetic or optical signals that carry digital data streams representing various types of information.

The network link 124 typically provides data communication through one or more networks to other data devices. For example, the network link 124 may provide a connection to another computer or remotely located presentation device through a local network 125 (e.g., an 802.11-compliant wireless network) or through equipment operated by a service provider, which provides communication services through a communications network 126. In preferred embodiments, the local network 124 and the communications network 126 preferably use electrical, electromagnetic, or optical signals that carry digital data streams. The signals through the various networks and the signals on the network link 124 and through the communication interface 123, which carry the digital data to and from the computer system 111, are exemplary forms of carrier waves transporting the information. The computer system 111 can transmit and receive data, including program code, through the network(s) 125 and 126, the network link 124 and the communication interface 123. Moreover, the network link 124 may provide a connection through a LAN 125 to a mobile device 127 such as a personal digital assistant (PDA) laptop computer, or cellular telephone. The LAN communications network 125 and the communications network 126 both use electrical, electromagnetic or optical signals that carry digital data streams. The signals through the various networks and the signals on the network link 124 and through the communication interface 123, which carry the digital data to and from the system 111, are exemplary forms of carrier waves transporting the information. The processor system 111 can transmit notifications and receive data, including program code, through the network(s), the network link 124 and the communication interface 123.

Other aspects of the invention may include data transmission and Internet-related activities. See Preston Gralla, How the Internet Works, Ziff-Davis Press (1996), which is hereby incorporated by reference into this patent application. Still other aspects of the invention may utilize wireless data transmission.

Figure 2:
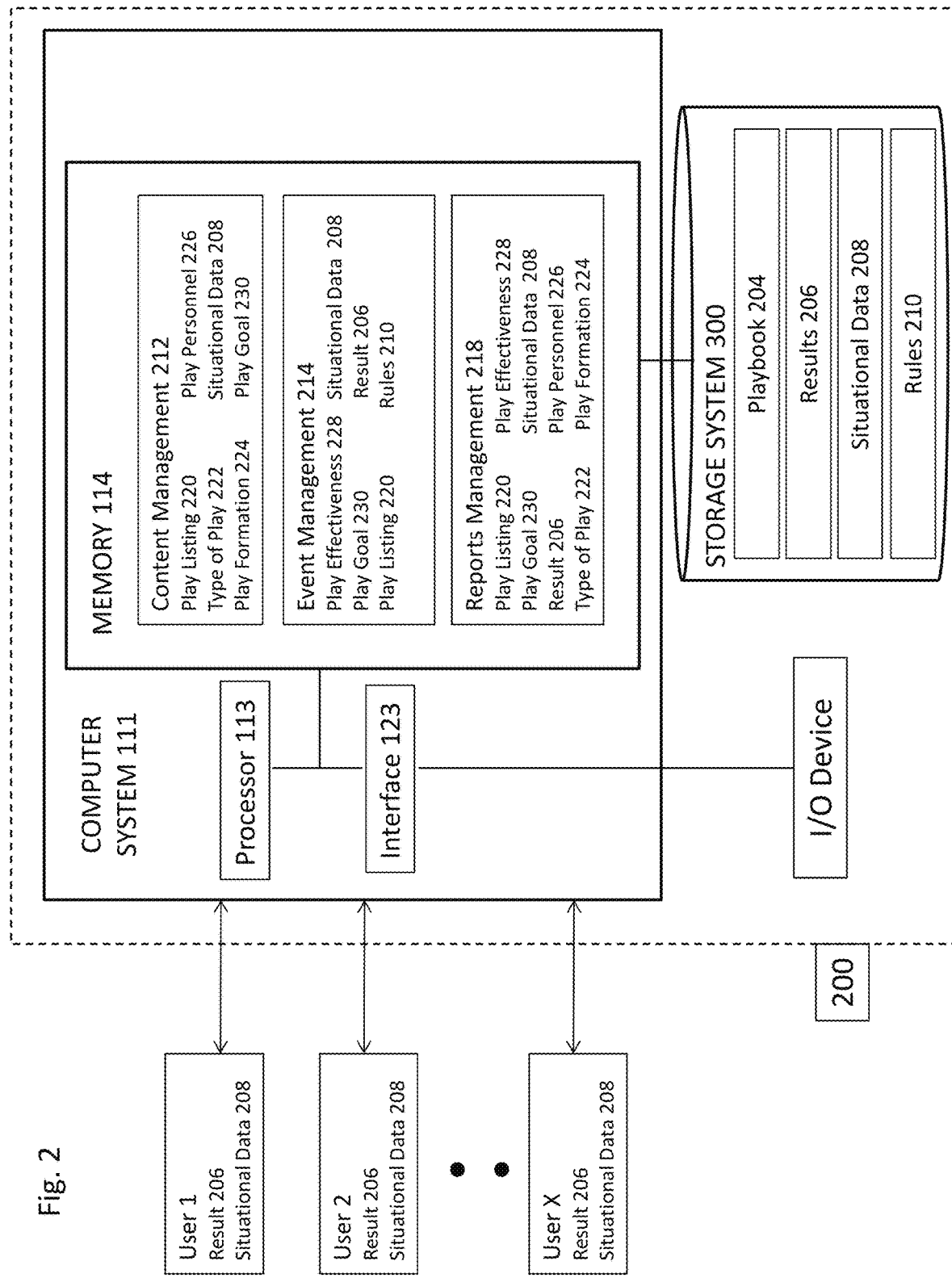
FIG. 2 is a diagram of an exemplary embodiment of the sports management system.

FIG. 2 shows an exemplary embodiment of a sports management system 200. System 200 can allow a user to plan, manage, and analyze a variety of aspects of a sports team, sporting event, or series of sporting events. System 200 can help a user determine which systems, plays or other actions may be effective or beneficial. System 200 can help to make these determinations based on data, for example data relating to the progress or outcome of a sporting event, that is input by one or more users. In some exemplary embodiments, system 200 can be utilized to plan, manage, and analyze any type of sporting event, for example a football game, basketball game, baseball game, soccer game, or any other type of sporting event as desired. While many of the examples contained herein pertain to American football, system 200 can be used to plan, manage, and analyze any type of sporting event or other scenario-based sequence of events.

System 200 can include content management function 212, which can allow users to upload data relating to players, plays, statistics, or any other content as desired. The content management function can allow users to organize or identify players or plays based on any desired attribute, such as chance of success, formation, game situation, players involved, or any other desired criteria. A search engine may also be incorporated into system 200 in order to allow users to parse the data stored therein.

Still referring to the exemplary embodiment illustrated in FIG. 2, content management function 212 can be configured to accept a wide variety of plays or schemes. For example, a user can upload a playbook 204, which can be a collection of many plays, into system 200. In some exemplary embodiments, a user can upload or input a playbook 204 relating to a "spread" type football offense, a "4-3" type football defense, or a "3-4" type football defense into system 200. A playbook 204 can be uploaded as a whole or it can be input by a user one play at a time. In some exemplary embodiments, as a user inputs a play, which may be in real time or after an event or game has happened, content management function 212 can prompt the user through a series of menus to input attributes associated with the play, for example the type of play 222, such as run or pass, the play formation 224, such as I-formation or shotgun, the play personnel 226, such as a package containing three wide receivers and two running backs, required for the play, or any other attribute as desired. In other exemplary embodiments, content management function 212 may determine or extract this information from playbook 204 once playbook 204 is uploaded into system 200.

Figure 3:
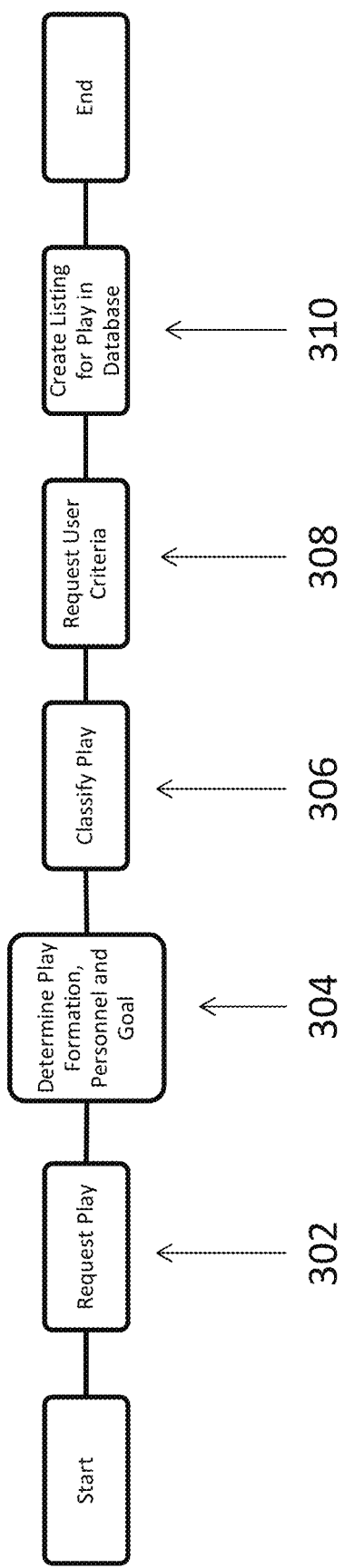
FIG. 3 is a flow chart of exemplary operational steps for entering information about a play into the system.

According to at least one exemplary embodiment, a method of inputting a playbook, such as playbook 204, may be depicted in exemplary FIG. 3. First, in step 302, system 200 may request plays to be input. Plays may be input in any desirable manner at any desired time, such as manually through prompts stored within system 200 or via any computer readable medium. Once plays are input into system 200, system 200 may determine, in step 304, the play formation 224, type of play 222, play personnel 226, or some combination thereof associated with each included play listing 220. Step 304 may be accomplished either by requesting the necessary information through prompts, such as drop-down or other menus, or by extracting such information from an uploaded or input playbook 204. For example, a user may input a running play by uploading a diagram and indicate that the play is a running play, utilizing an I-formation with two running backs, two receivers, and one tight end. Once this information is determined, content management function 212 can, in step 306, classify the input or uploaded play with regards to play type 222, play formation 224, play personnel 226, or any other desired attributes. Next, in step 308, content management function can request the user to input other attributes, for example play goal 230. Once this is complete, content management function can in step 310 create and store a record of this play within a database as a play listing 220, which may later be displayed to the user.

In this way, system 200 can facilitate analysis of plays regardless of the specific terminology used to describe them. Many different naming schemes can be used by many different teams, which can sometimes make cross-team analysis difficult. System 200 can allow plays or other information to be stored and organized based on standard attributes, which can facilitate statistical analysis despite differences in nomenclature.

Figure 10:
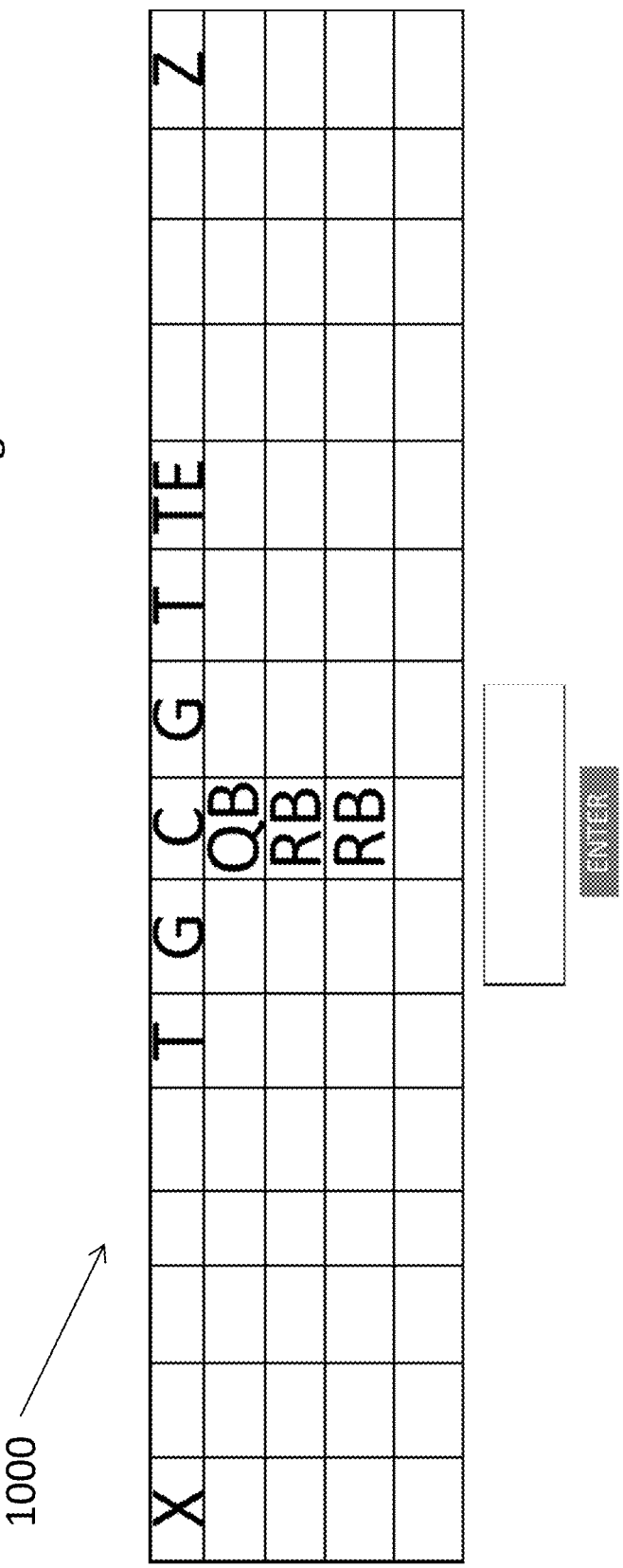
FIG. 10 shows an exemplary embodiment of a grid interface.

As one example, in the exemplary case of an American football team, plays can be entered and sorted by formation. FIG. 10 shows an exemplary embodiment of a grid interface that can be used to construct a play in order for it to be entered into system 200. In this grid interface, grid 1000 can be subdivided into cells which can represent every potential position available for a football formation. A user can describe a formation by associating a player with a cell corresponding to his or her position in the formation as it is lined up on the field. In this example, a Wide Receiver can be represented by X, Z, or B; a tight end can be represented by Y, a Tackle can be represented by T, a Center can be represented by C, a Guard can be represented by G, a Quarterback can be represented by Q, and a Running Back can be represented by RB. In this way, a team can analyze, for example, game film from another team and conduct effective statistical analysis and game planning despite differences in nomenclature or terminology.

Figure 4:
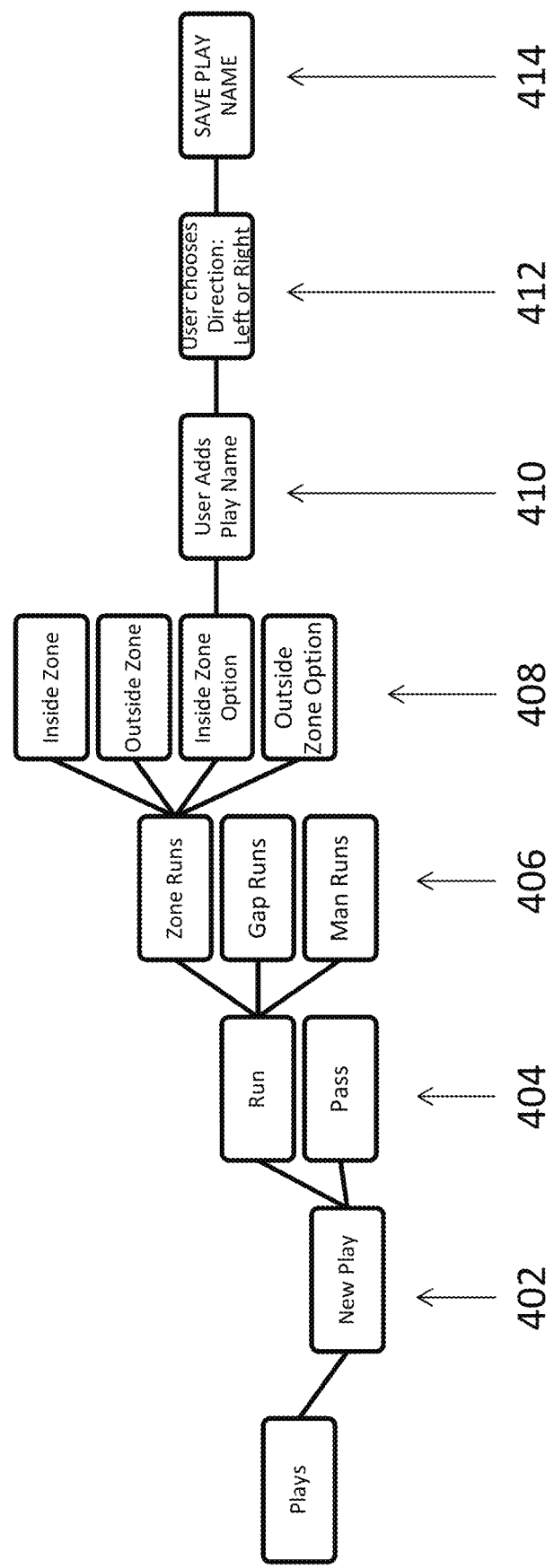
FIG. 4 is a flow chart of exemplary operational steps for entering information about a play into the system.

FIG. 4 shows a specific exemplary embodiment of a process through which a user can input a play, in this case a football running play. At step 402, the user can select New Play. At step 404, the user can be presented with options for type of play 222, and can select Run. At step 406, the user can be presented with options for attributes associated with Run plays, and can select Zone Runs. At step 408, the user can be presented with options for attributes associated with Zone Runs, and can select Inside Zone Option Runs. At step 410, the user can choose a name to be associated with this play in playbook 204. The user can finally choose a direction for the play at step 412 and save the play into the playbook 204 at step 414.

Regardless of how or when a user inputs, uploads, or otherwise enters plays or playbooks 204 into system 200, content management function 212 can create play listings 220 for each individual play contained within playbook 204. Play listings 220 may be identified by specific names or tags which the user assigns to the specific plays or by commonly used names which may be identified by the system. Play listings 220 can also be identified by attributes associated with the play, for example as type of play 222, play formation 224, play personnel 226 or play goal 230, or any other type of attribute as desired, for example directions and motions. As mentioned, content management function 212 can determine, extract, or otherwise glean this specific information from playbook 204 or may receive this information from user inputs, as received through any desired manner, such as a series of drop-down menus or user prompts as depicted in FIG. 4.

In some exemplary embodiments, once playbook 204 is uploaded or otherwise entered into system 200, a user can sort, or prompt system 200 to sort, the plays contained within playbook 204 based on various attributes, such as type of play 222, play formation 224 or play personnel 226. For example, content management function 212 may group together all plays which have been designated or selected as "pass" plays under type of play 222. Content management function 212 can also be used to sort plays by more than one attribute. For example, plays grouped together as "pass" plays in the attribute type of play 222 can be further sorted into play formation 224 groupings such as "shotgun" pass plays, or "I-formation" pass plays. Continuing this example further, the plays sorted under type of play 222 and play formation 224 can be further sorted by play personnel 226. For example, "pass" plays, "shotgun" plays and "I-formation" plays may each be sorted by the number of wide receivers on the field. Content management function 212 can interrelate any play listings 220 in any desired manner, such as those play listings 220 having similar characteristics, such as type of play 222, play formation 224, play personnel 226, play goal 230, or any other desired attribute or combination of attributes. Thus, for example, if a user desires a shotgun-type passing play with four receivers, content management function 212 can present all possible options.

Content management function 212 can also be used to store information regarding specific players or groups of players. Content management function 212 can, for example, store a player's name and number, as well as attributes associated with the player. These attributes can be, for example, a player's height, weight, speed, age or other physical qualities. Any other attributes can be associated with a player, for example the position played by the player, or a specific personnel grouping. In this way, a player stored by content management function 212 can also be associated with a play or group of plays in a playbook 204 by being included in a play personnel 226 attribute.

Referring again to FIG. 2, System 200 can also include an event management function 214. Event management function 214 can provide tools which can allow a user to strategize, manage, and evaluate an event as it happens. Examples of events that can be managed using event management function 214 can include games, practices, or any other type of event as desired.

In some exemplary embodiments, event management function 214 can be used to plan for games. Once system 200 has been populated with play listings 220, such as by uploading playbook 204 into system 200, a user can select certain plays for a specific game plan or opponent. Content management function 212 can sort the plays contained within playbook 204 before the user selects plays for a specific game plan and may present play listings 220 which may be preferred for the specific game plan, such as those play listings 220 which may be determined or denoted to be effective based on the schemes or tendencies of an upcoming opponent. Alternatively, a user may select any combination of play listings 220 for a game plan and select these play listings 220 to be the only plays presented during a specific game or sporting event. Further, either system 200 or a user may choose to interrelate specific plays with certain situational data 208 for a specific game or game plan. For example, if a user knows that his or her team's next opponent plays a defense such as a "tampa-2" type defense, the user may configure system 200 to only select plays effective against a tampa-2 defense during the upcoming game.

In some exemplary embodiments, event management function 214 can be used to construct tools which can be used during a game. For example, if a group of plays have been selected as appropriate for a particular game or opponent and incorporated into a game plan, event management function 214 can construct one or more ready sheets which can include a listing of those plays and other pertinent information. Multiple ready sheets can be constructed for each game plan as desired. For example, different ready sheets can be constructed for each different personnel grouping on a team, containing information appropriate for each personnel grouping. As an example, on a football team special ready sheets can be constructed for personnel groupings such as wide receivers, running backs, or linemen, each containing information that is especially useful for its intended audience. Additionally, other tools such as wristbands for quarterbacks can be constructed using event management function 214.

As an exemplary illustration of one embodiment of the system 200, a team can create a play call on their weekly ready sheet. The system 200 can assign a play call number to the play call for that week. That play call and play call number can be automatically mirrored on a quarterback wristband which can be generated by system 200. In this way, a coach is not required to type up a wristband, and the numbers can always be exactly the same on the ready sheet and wristband. This play call number can then be used to generate anything else such as practice scripts or game plans, or anything else as desired. When a play call number is entered, the corresponding play call can appear in the appropriate place on the script, wristband, game plan, or game data collector. In this way, system 200 can allow various items such as the ready sheet, the wristband, the practice scripts, the game plan, and the game data collector to be efficiently and easily created, organized, and analyzed.

Event management function 214 can be configured to accept or determine situational data 208. Situational data 208 can relate to any data which may traditionally be kept or stored in a scoreboard, scorecard or scorebook. Situational data 208 can relate to the time left in a sporting event, the quarter, period, or half which the game is in, the score, the number of timeouts each team has left, or any other desired data. For example, if it is being used to manage American football, event management function 214 can receive and determine situational data 208 relating to the time left in each quarter, the number of timeouts each team has left, which team has possession, and the down and distance remaining. Additionally, situational data 208 can relate to schemes or plays run by an opponent. In this way, event management function 214 can further evaluate play effectiveness 228 based on the scheme or play against which a play listing 220 is run. Situational data 208 may be entered in any desired manner, for example a series of prompts and drop-down menus.

Figure 5:
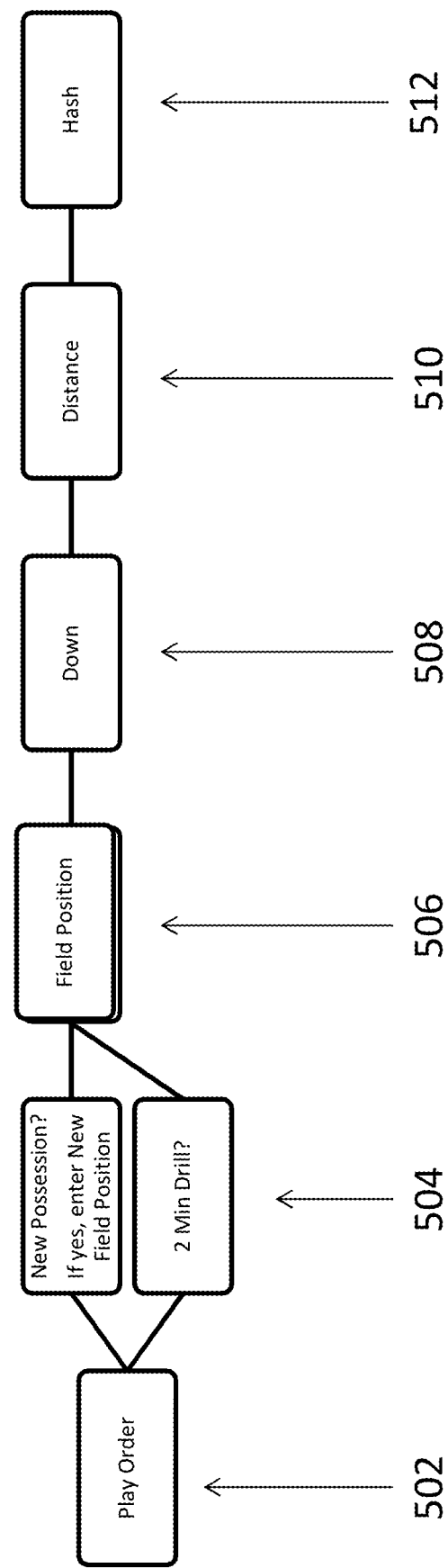
FIG. 5 is a flow chart of exemplary operational steps for entering situational data into the system

FIG. 5 shows an exemplary embodiment of a process for receiving situational data 208 relating to field position and down in an American football game. At step 502, event management function 214 can autofill the play order. At step 504, a user can indicate whether a 2 minute drill is necessary, and whether this is the start of a new possession. If a new possession is indicated, the user can enter the new field position. At step 506, the event management function 214 can either enter this new field position, or autofill new field position based on previous field position and the yardage of the previous play. At steps 508 and 510, event management function can autofill the new down and distance based on the previous play's down and distance compared to the yardage of the previous play, or enter first down and ten yards if this is a new possession. Finally, at step 512 the user can enter the hash necessary for the new play.

Once again referring to the exemplary embodiment depicted in FIG. 2, while a practice or game is occurring, event management function 214 can be configured to receive play results 206. After a play is run, a user may input results 206 into the system 200. Result 206 may be entered into the system through any keyboard or data entry device as desired, for example a touchscreen keyboard. Results 206 may relate to what transpired on the previous play and may allow system 200 to automatically update situational data 208 and determine the play effectiveness 228 of the prior play. For example, if the previous play resulted in a gain of seven yards, the user may input that the previous play resulted in a "gain" and when prompted for the number of yards, the user may enter "seven." This situational data 208 may allow system 200 to then determine situational data 208 relating to the next play. For example, if the gain of seven occurs on a first down and ten, system 200 may determine that the next play will be a second down play requiring three yards for a first down, in accordance with the rules 210 of American football. Results 206 can be entered or otherwise input into system 200 in any desirable manner, such as through a series of prompts and drop-down menus.

In order to determine play effectiveness 228, event management function 214 may compare play goal 230, which may be entered by a user or determined by content management function 212, to the result 206, which can be input by a user. In some exemplary embodiments, if a play listing 220 has a result 206 which has a value greater than that of play goal 230, the play listing 220 may be determined to be "effective." In other exemplary embodiments, system 200 may simply track the net yardage gain produced by a certain play listing 220 from result 206. In still other exemplary embodiments, evaluation system may determine play effectiveness 228 through any desirable statistical analysis or determine the effectiveness 228 of a play listing 220 when the play used in the presence of particular situational data 208. For example, if a team runs a passing play designed with a play goal 230 of gaining seven yards against a cover-2 defense and the play gains thirty-five yards, the play may be marked or otherwise designated generally effective, effective for gaining over twenty yards, effective against a cover-2 defense, five times more effective than expected, any combination thereof, or any desired variation. Each of these play effectiveness 228 determinations may be stored within system 200 and compared to other results 206, either previously or later recorded. In this way, event management function may create cumulative play effectiveness 228 determinations.

Still referring to FIG. 2, and although some exemplary embodiments may refer to or rely on post-event input, event management function 214 can be used to manage a game or other event while it is in progress. In some exemplary embodiments, event management function 214 can interrelate situational data 208, rules 210, and play effectiveness 228 relating to a particular play listing 220, in such a way that it can suggest effective play listings 220 to a user in any situation. System 200 may determine which plays are appropriate, effective or otherwise desirable for certain game situations based on the play effectiveness 228 of a play listing 220 in situations when similar situational data 208 was present. Further, event management function 214 can account for the rules 210 of the specific sport being played in order to ensure that effective play listings 220 are being displayed to the user. For example, if system 200 determines that a user's team is losing an American football game, has no timeouts left, and fewer than two minutes remain in regulation, system 200 may display a variety of shotgun passes with similar formations to increase the chance of scoring quickly and decrease the chance of unnecessarily using time for personnel substitutions and formation changes. Additionally, in other exemplary embodiments, system 200 may be able to provide situational suggestions or suggestions based on simulations or previously occurred events.

Event management function 214 can associate play effectiveness 228 with a specific play listing 220, such that a specific play may be recognized as effective for a certain result, such as gaining a certain number of yards. Thus, event management function can determine or select effective or otherwise desirable plays based on comparing situational data 208 to play effectiveness 228 in order to determine whether a play would be an appropriate selection at a particular time. For example, if a football team needs a play for third down with six yards to go, event management function can provide a user with plays effective for gaining six yards. Alternatively, a coach may ignore play effectiveness and request plays based on other attributes, such as type of play 222, play formation 224, play personnel 226, or any other attributes as desired. Further, a user may also input additional situational data 208 based on other criteria or circumstances, such as coaching decisions. For example, if a user decides to, if necessary, use four downs instead of the traditional three to try to gain a first down, the user may indicate this and event management function 214 can present third down play options which may be effective for gaining fewer yards than needed for a first down.

Figure 6:
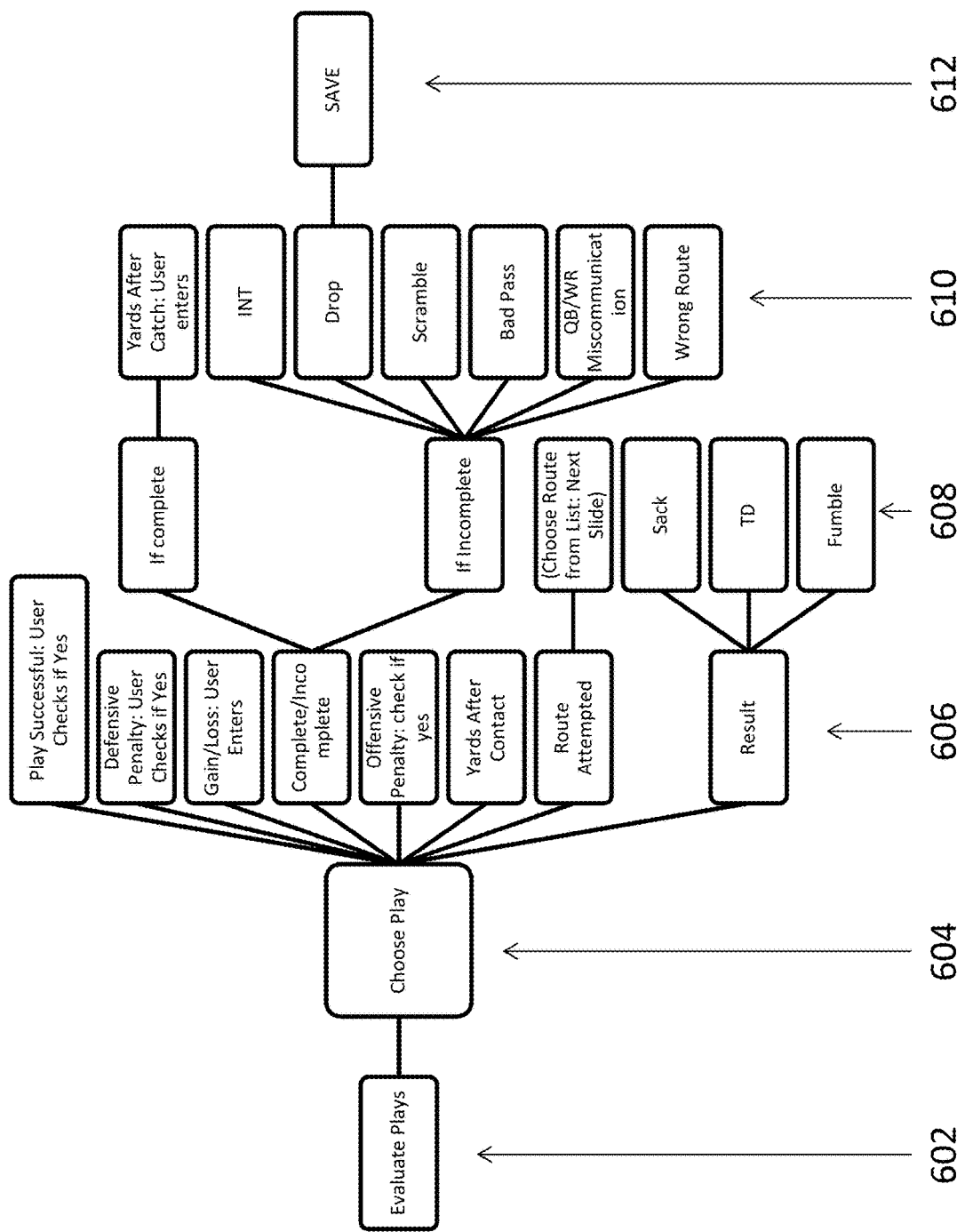
FIG. 6 is a flow chart showing exemplary operational steps for evaluating a play.

In some exemplary embodiments, event management function 214 can allow a user to input data relating to the result of a play in order to assist in evaluating the play. FIG. 6 depicts an exemplary embodiment of a series of menus which can allow a user to enter the result 206 associated with a play listing 220 into system 200 after the team attempts to execute a particular play listing 220. As depicted in FIG. 6, results 206 may relate to any aspect or action that occurred in the prior play. At step 602, the user can select Evaluate Plays. At step 604, the user can select the play that was run from a list of plays. At step 606, the user can enter information relating to the play, for example whether the play was successful, the amount of gain or loss, and whether a penalty occurred. At step 610, the user can provide further information, for example the yards run after a catch, or the reason that a pass attempt was incomplete. At step 612, the user can save the result 206 to content management function 212. Further, in some exemplary embodiments, results 206 may pertain to specific players as well as the play in general. In this manner, system 200 may not only evaluate the effectiveness of plays, but the effectiveness of the players acting within them.

Figure 7:
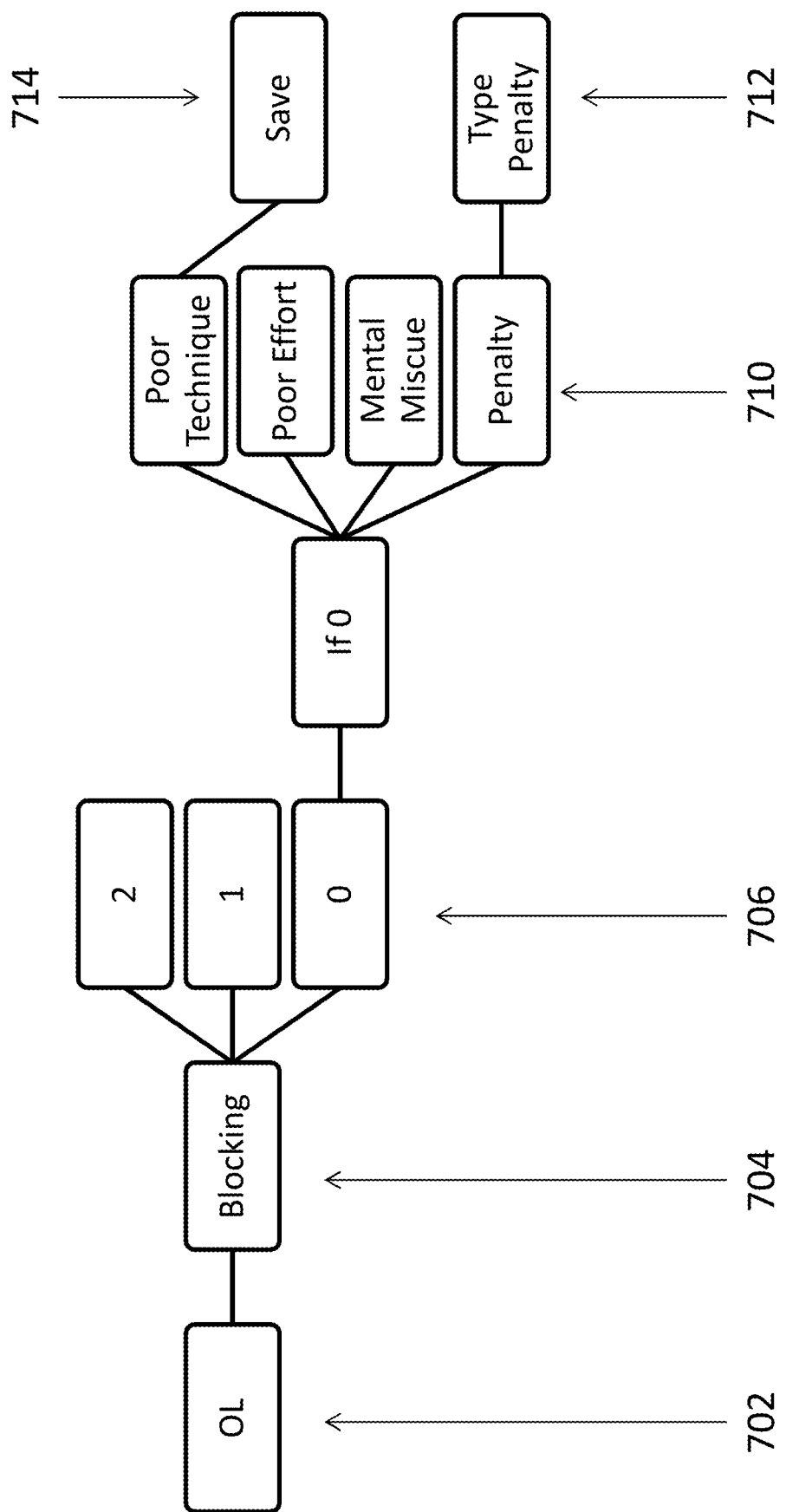
FIG. 7 is a flow chart showing exemplary operational steps for evaluating a player.

In an exemplary embodiment which allows event management function 214 to track the actions and effectiveness of the players themselves, system 200 may allow a user to input grades for the players. This data, similar to the data regarding a specific play, may also be stored in, for example, content management function 212, which can allow for further evaluation at a later time. FIG. 7 shows an exemplary embodiment of a series of menus which can allow a user to evaluate the performance of a player. At step 702, the user can indicate that the player is an offensive lineman. At step 704, the user can elect to enter information relating to the blocking performance of the player. At step 706, the user can select a grade corresponding to the performance of the player, for example 0. At step 710, the user can input a reason for the grade given, for example "poor technique" or "penalty." At step 712, the user can indicate the type of penalty. At step 714, the user can save the data to content management function 212.

Figure 8:
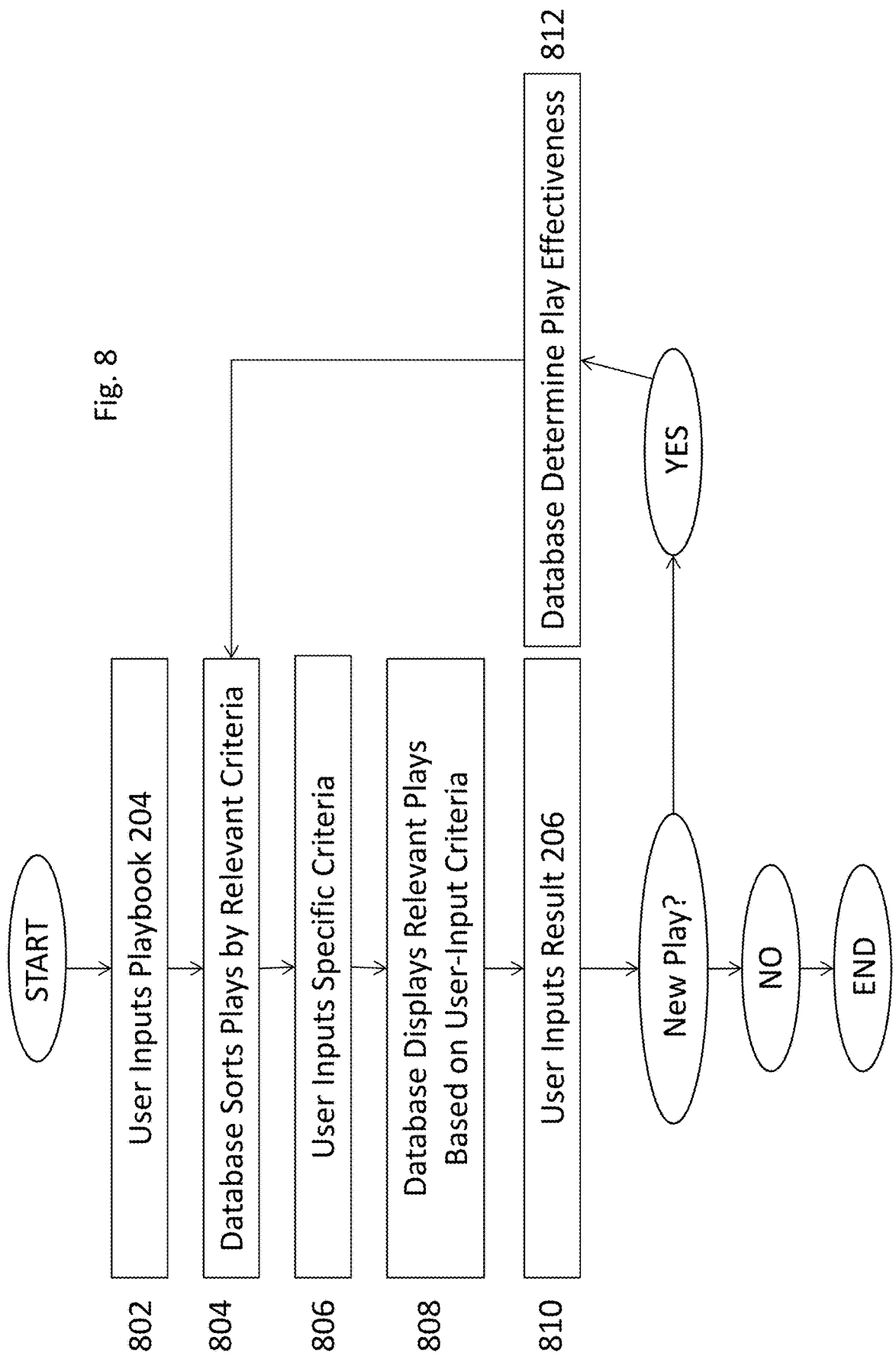
FIG. 8 is a flow chart showing exemplary operational steps for selecting a play.

FIG. 8 shows an exemplary process in which event management function 214 can facilitate the management of a game as it occurs. First, in step 802, a user can input a gameplan, which can consist of a playbook 204 or a subset of a playbook 204, into event management function 214. Once the gameplan is uploaded, system 200, which may include an integrated database, may sort, in step 804, the plays contained within the gameplan based on various criteria, such as type of play 222, play formation 224, play personnel 226, play effectiveness 228, or any other desired attribute. A user may then search this database based on specific criteria, in step 806, by inputting the specific criteria, such as play effectiveness 228. The system may then, in step 808, display relevant play listings 220, as determined based on the relevant criteria, game rules 210, and situational data 208. A user may select a play listing 220 from the play listings 220 displayed in step 608 and once the team runs the play, the user may input, in step 810, result 206 to reflect what occurred on the play.

Still referring to the exemplary method depicted in FIG. 3, once step 810 is complete, event management function 214 may reevaluate the plays based on the relevant criteria, but, in order to do so, play effectiveness 228 must first be determined in step 812. System 200 may determine play effectiveness by comparing play goal 230 to result 206, and may subsequently automatically update the play effectiveness 228 associated with the play listing 220 that was just run. At this point, system 200 may repeat step 804 and re-sort playbook 204 based on this updated data. Then, based on a user selection in step 806, system 200 may display the newly relevant play listings 220 in step 808. However, if a user declines to enter new criteria in step 806, system 200 may automatically update the play listings 220 shown to a user in step 808 based on the situational data 208 associated with the next play. The situational data 208 associated with the new or next play listings 220 may be determined, as shown above in FIG. 5, based on the previously existing situational data 208 and the results 206. This may be repeated until system 200 or a user determines that a new play is not needed.

In some exemplary embodiments, event management function 214 can be used to manage practices. Event management function 214 can be used to construct practice scripts, which can be specific list of play listings 220 in a particular desired order. FIG. 9 shows an exemplary embodiment of a practice script which is designed for a football offense. In this exemplary embodiment, element 902 can refer to the play number, element 904 can refer to the hash mark, element 906 can be the field position, element 908 can be the down, element 910 can be the distance, element 912 can be the playcall indicated on the quarterback's wristband, element 914 can be the play personnel 226 required for the particular play, element 916 can be the playcall, and elements 918, 920, and 922 can indicate the defensive alignment that is to be faced. These practice scripts can be used to construct ready sheets and other tools, and event management function 214 can suggest plays and receive data as described above and otherwise simulate a game environment.

While many of the aforementioned exemplary embodiments have discussed embodiments for monitoring and analyzing offensive American football plays, it is similarly envisioned that system 200 may be utilized to monitor and evaluate offensive and defensive plays, as well as, individual athlete performance, in any sport. In fact, in some exemplary embodiments, system 200 may combine these two functions in order to maximize the talents of a team by suggesting plays with specific players so that the play may be most effective. Additionally, system 200 may be used in any of a variety of conditions, such as real time input and analysis during an event or game, post-game input and analysis, and may work with simulation-based data, as desired.

Referring to FIG. 2, system 200 may also include report function 218. Report function 218 can generate in-depth statistical analyses of events that have been managed by system 200. These reports can be organized in a variety of ways, and be searchable and reconfigurable as desired. In some exemplary embodiments, these reports can, for example, help a user correlate the play effectiveness 228 of a play listing 220 with its corresponding situational data 208 in order to assist a user in understanding the reasons for a result and strategizing for the future.

In an exemplary embodiment in which a system 200 is used to manage an American football team, a variety of reports can be generated. For example, report function 218 can generate reports relating to a single game or practice, a season of games or practices, or any other desired combination. The reports can present information in the form of graphs, lists, percentages, or any other format as desired. The reports can come in a variety of forms. For example, report function 218 can generate a Tendencies Summary, which can give a user a breakdown of the actions he or she took, for example running the ball or passing the ball, when confronted with a specific set of circumstances. Report function 218 can also generate a Success Rate Summary, which can indicate the total number of results and the success rates of specific actions, for example specific plays or types of plays. In some exemplary embodiments, the Success Rate Summary can indicate, for example, the number of yards gained or lost on average by individual play listings 220. Report function 218 can also generate lists of particularly successful or particularly unsuccessful plays or types of plays, organized by result or success rate.

In some exemplary embodiments, report function 218 can also generate reports based on situational data 208. For example, report function 218 can generate a summary of actions taken and results achieved in specific situations. As an example, report function 218 can create a report listing every play called on any specific down, distance, field position, time remaining, hash mark, or any other situation or combination of situations as desired.

In other exemplary embodiments, report function 218 can also generate reports for specific players or personnel groups. For example, separate reports can be generated for the offense and defense of a football team, and those reports can be further subdivided by personnel grouping. Reports can also be generated organized by, for example, formations used, defensive fronts and coverages shown, motions, shifts, or stunts employed, or blitz packages used.

In still other exemplary embodiments, report function 218 can provide reports about specific players. The reports can include information such as the number of games, practices, plays, type of plays, situations, personnel packages, and actions in which the player was involved, as well as the result in each case. The reports can focus on the player's statistics relating to certain actions, for example throwing, receiving, blocking, blocking, running, or blitzing.

Each of the functions discussed above can be executed for the entire team, or separately for any desired subdivision or combination of subdivisions of a team. For example, separate playbooks 204 can be stored for the offense and defense of a team. Separate gameplans, practice scripts, and ready sheets can be constructed for, as an example, the offense, defense and kicking unit. After practices or games, separate reports can be generated, or reports can be combined in any configuration as desired.

The system 200 can be implemented using any type of input or output device as desired. In some exemplary the system 200 can be a web based application which can make use of an internet connection, which can allow any device connected to the internet to use it. In one exemplary embodiment, the system 200 can be implemented on one or more tablet or laptop computers. As an example, a team could use multiple tablet computers for multiple coaches. In this example, the separate tablets used by the different coaches could each be used to manage the playbooks 204, gameplans, practice scripts, ready sheets, evaluations, and reports appropriate for each coach. Further, in this example the tablet computers could be capable of communicating with each other as well as the system 200 as a whole. As a result, any sort of communication between any user of the system and any other user could be facilitated. In this way, a head coach could access, for example, the gameplans prepared by his or her assistant coaches, and provide approval or corrections as required. Or, as another example, a coordinator could assemble a practice script, disseminate it to the position coaches within his or her purview, and then keep track of the progress of each unit throughout the practice using reports generated by his or her assistants.

Further, in some other exemplary embodiments, the system 200 can be utilized to compare various items, such as playbooks 204 or data generated by report function 218. In such embodiments, groups of plays and situations, for example, may be compared in order to provide statistical data amongst multiple teams, multiple sets of playbooks or any other data utilized in the system 200, as desired. In some exemplary embodiments, where there is video data of plays, system 200 may be utilized to automatically create video overlays of the same play run in different scenarios, but associated with the same situational data. For example, video overlays can be created for situations where the team is losing with two minutes remaining in a game (or in an equivalent situation simulated in practice), and a particular play is run, and then tabulate the success rate of the play.

System 200 may utilize video overlays to determine if the positioning of a player or players affected the play, the movement or speed of the players or ball affected the success of the play, and the like. Such video overlays may be stored in a database or cloud based memory (as described below), but may also be selected and displayed to a viewer upon request. For example, a coach could review a play run in practice based on certain situational data and overlay that with the same play run during a game and evaluate, for example, both visually and with metrics output by system 200, why different successes or failures occurred.

In still other exemplary embodiments, event management function 214 can be used for real time strategy and providing situational outputs and recommendations for a user. For example, if a user is presented with a certain set of situational data 208, event management function 214 can provide an immediate output of a play from the playbook that is most likely to be successful in that situation, or a listing of a group, for example four plays, with the highest likelihood of success. In this example, the situational data 208 may include the time in the game (for example two minutes left in the fourth quarter of a football game), the score, the down, the location on the field, the status of players (e.g. if the best wide receiver has been injured and is not available to play, or if a player has an injury that still allows them to play, but at a degraded performance), and the defense that the opponent is utilizing. The user may enter this information on the input/output device and the system 200 may then immediately provide an output on the display of the input/output device of one or more plays that would have the highest likelihood of success (for example getting a first down, getting to a desired field position, or scoring), the player personnel data that is needed, and the formation. In some exemplary embodiments, the historical success rates of such plays may also be shown.

It can be appreciated that the output of the plays with the highest rate of success can also be tailored, as desired. For example, in some situations, the success rate of the plays and outputted play choice or choices may be determined based on historical data from previous games during a single season or multiple seasons. In other situations, the success rate of plays and output play choice or choices may be determined based on games played against the same opponent or similar opponents during that season or previous seasons. In still other examples, the success rate of the plays and outputted play choice or choices may be based on practice data related to plays conducted in the days leading up to the game. In still other examples, success rate of the plays and outputted play choice or choices may be based on data calculated from just the current game being played. Additionally, in other examples, the success rate of the plays and outputted play choice or choices may be made from any combination of factors recited above.

In such exemplary embodiments, a real time interpolation of stored play data with respect to situational information is used to provide a user (or coach) with appropriate play selection, along with personnel decisions, formation information, and the like. Without the system as described in the exemplary embodiments herein, such determination of appropriate play outputs and decisions would be impossible.

In other words, the amount of play data stored in the database described herein will may be in the thousands of plays, the review of which by a coach (or other personnel) would require hundreds of hours of viewing time. Moreover, in order to draw any meaningful conclusions from the data in the absence of embodiments described herein, the viewer would have to manually select and view both game play data and practice play data to make comparisons between player activities and actions. However, still further time would need to be used in order to account for situational data. Given the specific time constraints associated with sports seasons, where there may only be a few days between games, such review by itself would be impossible. Moreover, it would be impossible for a human reviewer to extract much meaningful information in the limited timeframe, much less have the ability to do it in real time during a game or practice situation.

In still other exemplary embodiments, player effectiveness and/or the effects of injuries on players may be determined using system 200. In these exemplary embodiments, the results of plays may be stored, as above. However, the tasks performed by individual players may also be tracked and evaluated. Thus, if a player blocked a first defender on a play and it was successful, that may be compared to a player blocking a second defender on a later version of the play. The results of the two plays can then be compared based on the tasks performed by that player. Other tasks could involve going in motion, running a certain route, shifting, or the.

Further, over the course of numerous plays, if there is known injury affecting a certain player, the effectiveness or success rate of the plays can be measured against the same or similar plays made before a player was injured. A variation in the success rates of these plays can then show how much the injury affected the player and overall success rate of the team. For example, if a team runs a set of plays X when playing team ABC in a first game and player 1 is uninjured in that game, but player 1 has a minor injury (for example a sprained ankle) in a following game, the results of the set of plays X in the first game against team ABC can be measured against the set of plays X in the second game against team ABC. The success rate of the plays can then be interpolated as a result of the injury to player 1, or it may be shown that player 1 has little effect on the success rate of plays, depending on the comparison.

When such an evaluation is made, the system 200 can provide an output shown as an effectiveness rating for the player or and injury effect rating on the player. Such outputted ratings can then be used in the situational data to help prompt a user of system 200 and provide an improved determination of plays to run in different situations, as outlined above. Such information could also be utilized to automatically select player personnel packages for a user of system 200.

Figure 11:
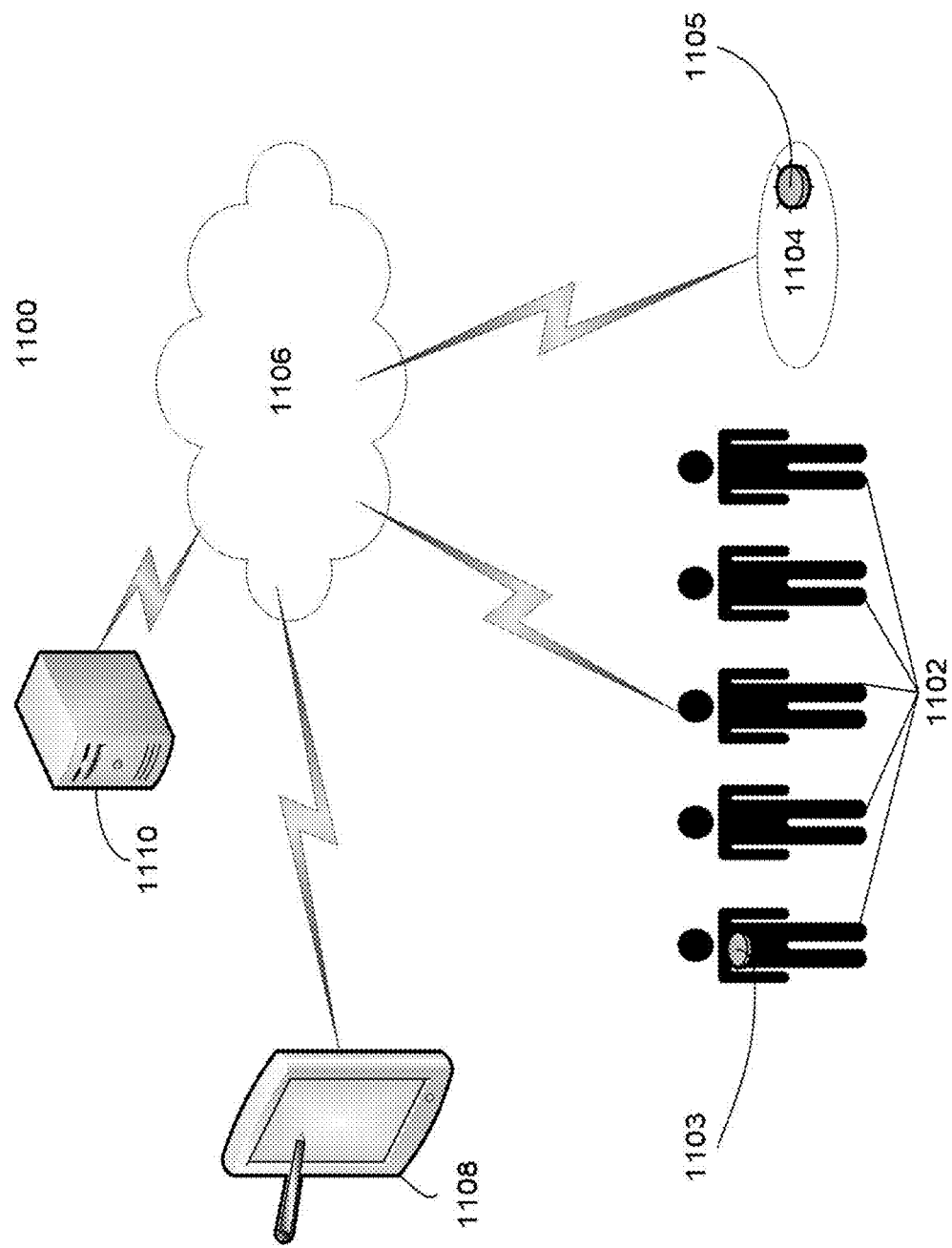
FIG. 11 shows an exemplary embodiment of a real time situational analysis and assistance tool.

Referring now to exemplary FIG. 11, another embodiment of a tool for analyzing situations and scenarios and outputting plays with the highest probability of success may be shown. In this exemplary embodiment, system 1100 may be similar to system 200 described above. However, here system 1100 may be utilized in real time during a game, such as a football game. The system may include any number of players 1102. Each player 1102, in some exemplary embodiments, may have a tracking device 1103, such as an RFID tag, GPS chip, or other such device embedded on their uniform. Additionally, in some exemplary embodiments, ball 1104 may have a similar tracking device 1105 embedded therein. These devices may be used to track player and ball movement during the course of a play in real time. As a result, the location of the players, their movement and speed of movement, and the progress of the play (such as gaining a certain number of yards or scoring), may be tracked during each play. It may be appreciated that a field on which the game is being played may also include embedded sensors for tracking the movement of players 1102 and/or the ball 1104. Alternatively, sensors otherwise positioned proximate or near the field of play, remotely located scanners, satellites, or the like can also be used to track the movement of players 1102 and the ball 1104.

However, in some alternative exemplary embodiments, it is envisioned that system 1100 may be utilized without tracking devices 1103 and 1105, as well as any related sensors. In such situations the player movements, formations, plays, and the like may be inputted by one or more users observing the play or watching a replay, may be made automatically using video tracking capabilities or other movement and analysis tools. Additionally, in some exemplary embodiments where system 1100 is being utilized, upon selection of a play, formation, player personnel package, or the like using computing device 1108, this information may be automatically stored and/or transmitted to the cloud 1106 and server 1110 to provide automatic data population and render the analytics performed by server 1110 as being made based on real time or active game data with the current opponent.

Still referring to exemplary FIG. 11, once a play is underway, the movement of the players 1102 and ball 1104 may be tracked. This information may be uploaded to cloud 1106. Cloud 1106 may be communicatively coupled to server 1110 which may perform real time analysis on the result of the play based on the movement of players 1102 and ball 1104. Server 1110 (or cloud 1106) may also be synchronized with game situational data, such as the time of the game, the score, location on the field, weather conditions, and the like which may affect the choice of play utilized.

Upon the completion of a play, the data is sent to cloud 1106 for storage and server 1110 performs the comparative analysis of the play, as described previously. Further, server 1110 will utilize the result of the play, the situational data, and other analysis and data described herein to transmit data to a computing device 1108, such as a tablet. Device 1108 may be utilized by a coach or other authorized personnel at the game described with respect to FIG. 11. The transmitted data from server 1110 to device 1108 may include the most successful play options for the next play, based on the analytics performed by the server 1110. Additionally, the transmitted data can include the likelihood of success of the play contained in the transmitted data. Further, the transmitted data may include a number of plays, for example four plays, with the related likelihoods of success of each of those plays. The coach may select a desired play on device 1108, which allows the play call to be sent to the cloud 1106 and ultimately to server 1110 for appropriate analysis following the completion of the play. Additionally, the selection of a play on device 1108 may also affect the transmission of the desired play to a designated player or players among players 1102, who can receive the play information through a communication device, display device, or the like that may be positioned on or otherwise associated with players 1102. The play data may also provide any other desired information, such as formation, audible options and their success rates, or other data related to the particular situation so that the players 1102 can rapidly see and review the data and then proceed to execute the desired play.

In such an example, the system 1100 is effectively translating data regarding large amounts of historical plays, both from games and practices, and outputting a specific play or plays based on the analytics performed. As described herein, such data would be impossible for a coach or other personnel to obtain and perform within the confines of a game or even within typical time between games. Thus, the system allows for compiled historical data, which would otherwise be useless or of limited use to be quickly processed and translated into specific outputs as guidance and recommendations that can be immediately utilized by a coach or team.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A system comprising:
   a computing device configured to receive data, wherein the data comprises at least one of situational data, player data, play data, and opposing team data;
   a storage device communicatively coupled to the computing device and configured to store a play tree structure comprising a plurality of plays and a plurality of levels, wherein a first level of the play tree structure comprises a plurality of play options and a second level of the play tree structure comprises a plurality of further attributes associated with each of the plurality of play options, and store data from one or more previous games; and
   an input device configured to accept input from a user and store the input in the storage device, wherein the computing device is configured to compare data of a current game to data stored in the storage device from the one or more previous games to identify one or more plays with a chance of success, present one or more plays selected from the plurality of plays and the chance of success associated with each selected play, after presenting each selected play, provide a nested menu interface to the user on the input device and receive, from the nested menu interface, at least one play type from a first interface dialog, provide a plurality of second interface dialogs based on a selection from the first interface dialog, and receive at least one augmentation to the at least one play type from a selection of a second interface dialog, and present a further one or more plays based on at least one user-specified play result.

2. The system of claim 1, wherein the computing device is further configured to use the data from the one or more previous games to determine the chance of success associated with each selected play, and use the data of the current game to determine a next play which will have the chance of success.

3. The system of claim 1, wherein the play data comprises at least one of a formation, play effectiveness, a type of play, and players involved in the play.

4. The system of claim 1, further comprising:
   a network link communicatively coupled to a plurality of user devices.

5. The system of claim 1, wherein, after the current game ends, the computing device is configured to store the game data of the current game into the storage device along with the game data relating to the one or more previous games.

6. The system of claim 1, wherein a play goal is related to a play and the computing device is further configured to determine play effectiveness by comparing the play goal to a result of the play.

7. The system of claim 2, further comprising:
- a playbook stored on the storage device, wherein the computing device is further configured to sort plays contained within the playbook and present plays which are preferred for a specific game play based on tendencies of an opponent.

* * * * *